US009086093B2

(12) United States Patent
Metrikin

(10) Patent No.: US 9,086,093 B2
(45) Date of Patent: Jul. 21, 2015

(54) ANGULAR CONTACT BALL BEARING

(71) Applicant: New Hampshire Ball Bearings, Inc., Chatsworth, CA (US)

(72) Inventor: Alex Metrikin, Los Angeles, CA (US)

(73) Assignee: NEW HAMPSHIRE BALL BEARINGS, INC., Chatsworth, CA (US)

( * ) Notice: Subject to any disclaimer, the term of this patent is extended or adjusted under 35 U.S.C. 154(b) by 60 days.

(21) Appl. No.: 13/767,013

(22) Filed: Feb. 14, 2013

(65) Prior Publication Data
US 2014/0226928 A1    Aug. 14, 2014

(51) Int. Cl.
F16C 33/38      (2006.01)
A61C 1/18       (2006.01)
F16C 19/18      (2006.01)
F16C 19/55      (2006.01)
F16C 33/44      (2006.01)

(52) U.S. Cl.
CPC ............. *F16C 33/3806* (2013.01); *A61C 1/181* (2013.01); *F16C 19/182* (2013.01); *F16C 19/55* (2013.01); *F16C 33/385* (2013.01); *F16C 33/3856* (2013.01); *F16C 33/44* (2013.01); *F16C 2206/40* (2013.01); *F16C 2240/30* (2013.01); *F16C 2240/40* (2013.01); *F16C 2316/13* (2013.01)

(58) Field of Classification Search
CPC .. F16C 19/16; F16C 19/163; F16C 33/38337; F16C 33/3843; F16C 33/3856; F16C 33/3806; F16C 33/385; F16C 2240/30; F16C 2240/40; F16C 2316/13

USPC .................. 384/470, 523, 527, 528, 572, 576
See application file for complete search history.

(56) References Cited

U.S. PATENT DOCUMENTS

| 1,915,287 | A | * | 6/1933 | Bott ............................. 384/528 |
| 3,096,129 | A | | 7/1963 | Hay |
| 3,647,269 | A | | 3/1972 | McKee |
| 4,932,500 | A | | 6/1990 | Smith et al. |
| 5,522,667 | A | * | 6/1996 | Miyake ......................... 384/492 |
| 6,443,623 | B2 | | 9/2002 | Sugita et al. |
| 6,599,124 | B2 | | 7/2003 | Nakanishi |
| 6,634,792 | B1 | | 10/2003 | Gorenne et al. |
| 6,742,934 | B2 | * | 6/2004 | Matsuyama et al. .......... 384/572 |
| 7,059,776 | B2 | * | 6/2006 | Kobayashi et al. ........... 384/470 |

(Continued)

OTHER PUBLICATIONS

International Search Report and Written Opinion date Jun. 10, 2014).

*Primary Examiner* — James Pilkington
(74) *Attorney, Agent, or Firm* — Grossman, Tucker, Perreault & Pfleger, PLLC

(57) ABSTRACT

An angular contact bearing including an inner ring and an outer ring. Each ring includes a raceway. A plurality of balls are in rolling contact with the raceways. The bearing includes a retainer having a width being the distance between a first side and a second side of the retainer, an outer surface extending between the first side and the second side and an inner surface opposing the outer surface. The retainer also has a central portion having a first thickness $T_1$, and tapered portions each having a second thickness $T_2$. Each tapered portion 1) extends from one of said sides to said central portion up to 28% of the length of said retainer width, 2) tapers towards the inner surface of the retainer at an angle of 20° or less relative to said central portion, and 3) tapers away from the inner diameter surface of the outer ring.

21 Claims, 9 Drawing Sheets

(56) References Cited

U.S. PATENT DOCUMENTS 7,364,365 B2  4/2008  Begin
8,172,462 B2  5/2012  Suzuki et al.
2005/0063627 A1  3/2005  Ueda et al.
2011/0069920 A1*  3/2011  Aida .............................. 384/572
2011/0299805 A1  12/2011  Damato et al.

* cited by examiner

ANGULAR CONTACT BALL BEARING

FIELD

The present disclosure relates to angular contact ball bearings and, in particular, to angular contact ball bearings that may be employed in relatively high speed applications including, for example, high speed dental handpieces working at speeds of up to 500,000 rpm.

BACKGROUND

Angular contact ball bearings are generally selected for applications wherein loading occurs in both the axial and radial directions. These bearings may be used in relatively high speed, precision applications including, for example, dental applications, turbo chargers, electric motors, automotive applications, pumps and compressors. However, problems remain due to bearing retainer wear, which is generally understood to be the one of the leading causes of a high speed bearing failure.

For example, retainers used in high speed applications, such as high speed dental handpieces, may be piloted (guided) by the inner or outer bearing ring land surfaces, requiring physical contact between the retainer, formed of a relatively softer material, such as a polymer resin, and the bearing ring land surface, formed of a relatively harder material. Guiding is specifically necessary in the bearings working at extremely high speeds, for example in dental handpieces rotating with the speeds up to 500,000 RPM, to minimize and limit uncontrollable otherwise retainer vibrations. Guiding requires a physical contact between the retainer and ring causing the retainer to wear. Therefore, a need still remains in the bearing industry to avoid or minimize retainer wear that could ultimately lead to premature failure.

SUMMARY

An aspect of the present disclosure relates to an angular contact ball bearing. The angular contact ball bearing includes an inner ring having an outer diameter surface and a raceway defined in the outer diameter surface and an outer ring including an inner diameter surface and a raceway defined in the inner diameter surface. Further, the angular contact ball bearing includes a plurality of balls in rolling contact with the raceways. In addition, the bearing includes a retainer having a first side and a second side opposing the first side. The retainer has a width being the distance between said first side and said second side. The retainer also has an outer surface extending between the first side and the second side and an inner surface opposing the outer surface extending between the first side and the second side. The outer surface and inner surface of the retainer define a central portion having a first thickness $T_1$, and tapered portions each having a variable second thickness $T_2$. Each tapered portion (i) extends from one of the sides to the central portion up to 28% of the length of said retainer width, (ii) tapers towards the inner surface of the retainer at an angle of 20° or less relative to said central portion, and (iii) tapers away from the inner diameter surface of the outer ring. Further, the second thickness $T_2$ of the retainer is less than the first thickness $T_1$, wherein $T_2<T_1$. In addition, the retainer includes a plurality of through holes, commonly known as ball pockets, defined in the retainer, wherein one ball is positioned in each of the ball pockets in a rotatable manner.

In another aspect, the present disclosure relates to an angular contact bearing. The bearing includes an inner ring including an outer diameter surface, and a raceway defined in the outer diameter surface, and an outer ring including an inner diameter surface, and a raceway defined in the inner diameter surface. The bearing also includes a plurality of balls in rolling contact with the raceways and a retainer. The retainer includes a first side and a second side opposing the first side, the retainer having a width being the distance between the first side and the second side. The retainer also includes an outer surface extending between the first side and the second side and an inner surface opposing the outer surface extending between the first side and the second side. The outer surface and the inner surface define a central portion having a first thickness $T_1$, and tapered portions each having a second thickness $T_2$. Further, each tapered portion: (i) extends from one of the sides to the central portion at least 11% of the length of the retainer width or more; (ii) tapers towards the inner surface of the retainer; (iii) tapers away from the inner diameter surface of the outer ring, and the second thickness $T_2$ is less than the first thickness $T_1$ wherein $T_2<T_1$. Finally, a plurality of through holes are defined in the retainer, wherein one of the balls is positioned in each of the through holes in a rotatable manner.

In a further aspect, the present disclosure relates to the incorporation of the angular contact bearing in a dental handpiece.

BRIEF DESCRIPTION OF THE DRAWINGS

The above-mentioned and other features of this disclosure, and the manner of attaining them, may become more apparent and better understood by reference to the following description of embodiments described herein taken in conjunction with the accompanying drawings, wherein.

DETAILED DESCRIPTION

The present disclosure relates to angular contact ball bearings and, in particular, to angular contact ball bearings that may be employed at relatively high speed in dental handpieces operating at speeds up to 500,000 revolutions per minute. Although reference is made to the use of the angular contact ball bearing herein in connection with such application, the invention herein is more broadly directed at reducing retainer-outer ring contact and overall retainer friction and wear.

As noted above, bearing retainer (i.e., cage, separator) wear is understood to be one of the single leading causes of bearing failure. Since the bearing works at the extremely high speed, retainer dynamic stability is desirably maintained to avoid retainer uncontrollable vibration causing undesirable handpiece noise and accelerated wear. One of the ways to minimize retainer vibration is piloting or guiding it by means of designing it with dimensions resulting in the retainer rotating in the close proximity to the piloting land. The retainer can be piloted either by the inner ring land or outer ring land. Piloting the retainer by an outer ring land is preferable due to the fact that inner ring rotational speed is near 2.5 times faster than the retainer speed in the bearing size typical for the most high speed dental handpieces. Therefore, less wear is seen on a retainer surface when it is piloted by an outer ring land. However, some wear still exists.

Figure 1:
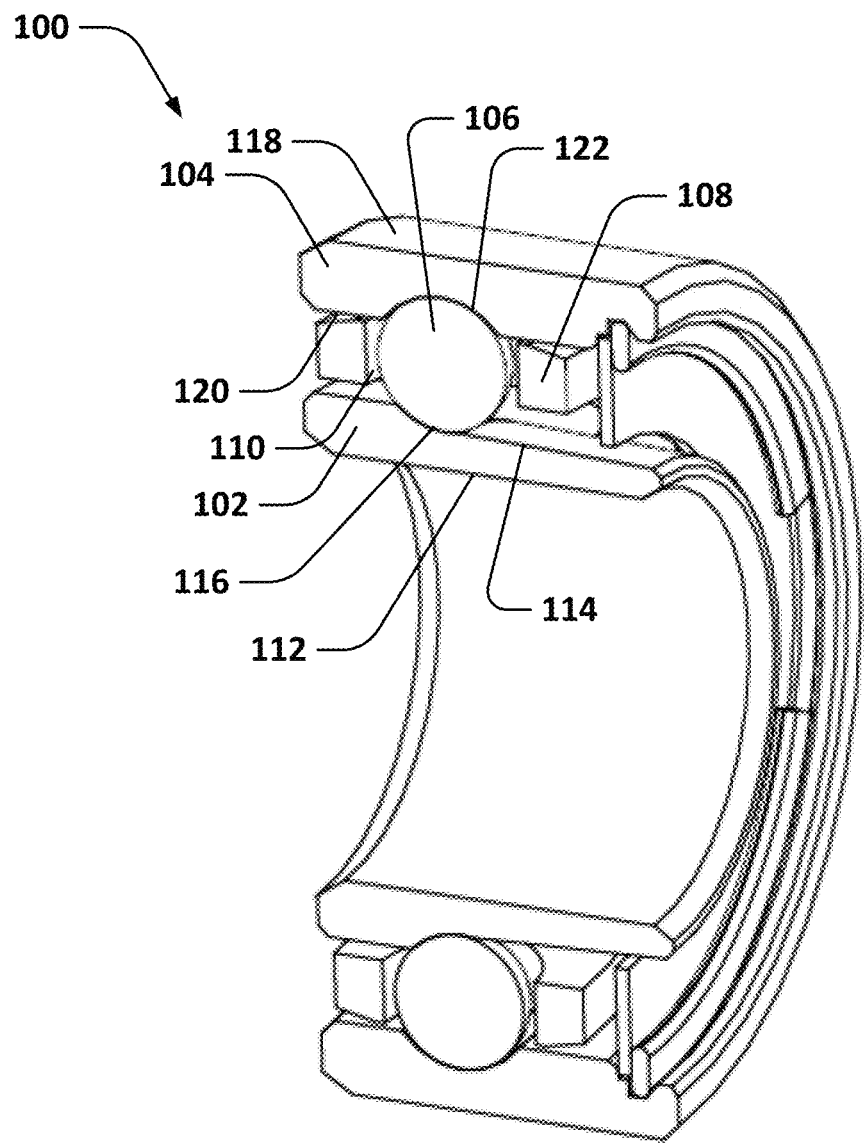
FIG. 1 is a cross-sectional perspective view taken along the diameter of an embodiment of a bearing contemplated herein.
Figure 2:
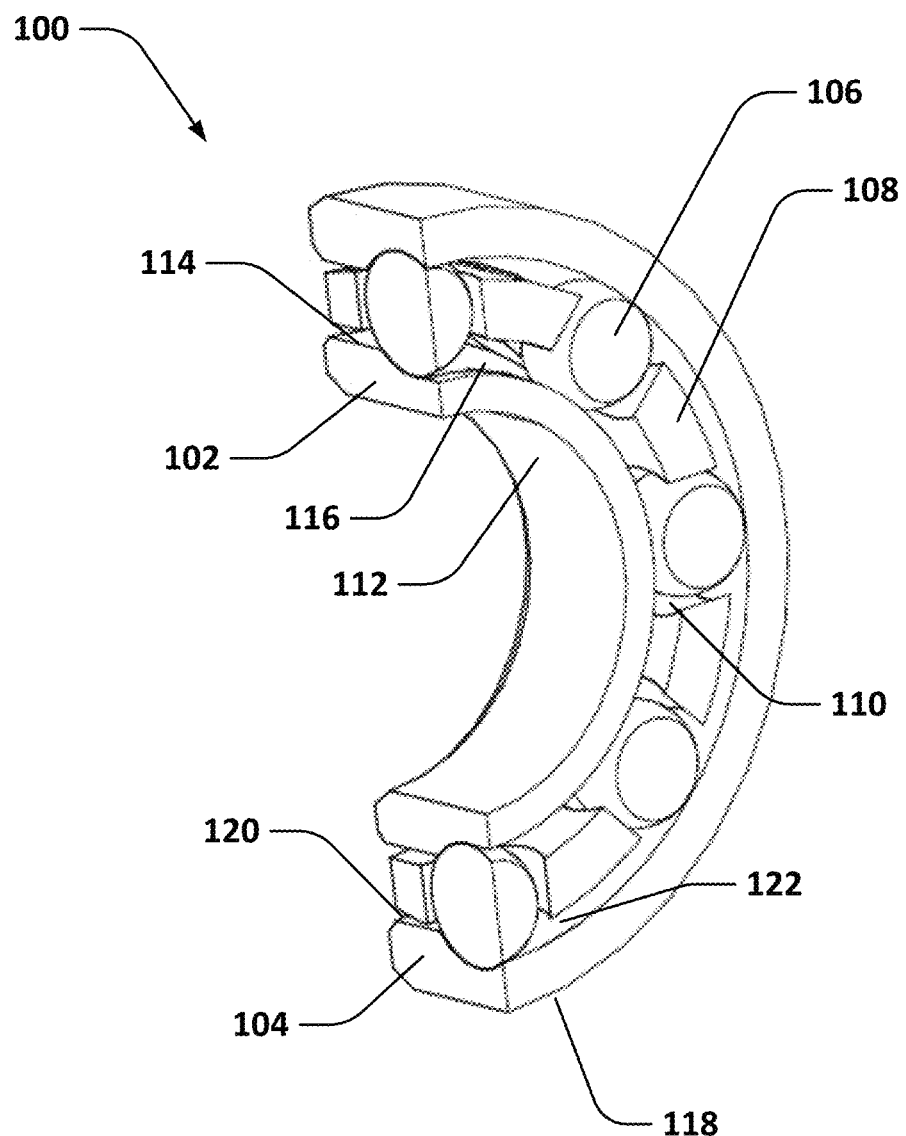
FIG. 2 is a sectional view illustrating cross-sections taken along the diameter and through the thickness of the bearing of FIG. 1.

FIGS. 1 and 2 illustrate an embodiment of an angular contact ball bearing 100. The bearing 100 is generally circular in shape and includes an inner ring 102, an outer ring 104, a plurality of balls 106 in rolling contact with said rings, and a retainer 108 including ball pockets 110, through holes defined in the retainer, therein for spacing the plurality of balls 106 around the diameter of the bearing. The inner ring 102 includes an inner diameter surface 112, an outer diameter surface 114, and an inner raceway 116 defined in the outer diameter surface 114 of the inner ring 102. The outer ring 104 includes an outer diameter surface 118, an inner diameter surface 120, and an outer raceway 122 defined in the inner diameter surface 120. The inner and outer raceways partially retain the plurality of balls 106 in a rotating manner relative to the bearing surfaces.

Figure 3:
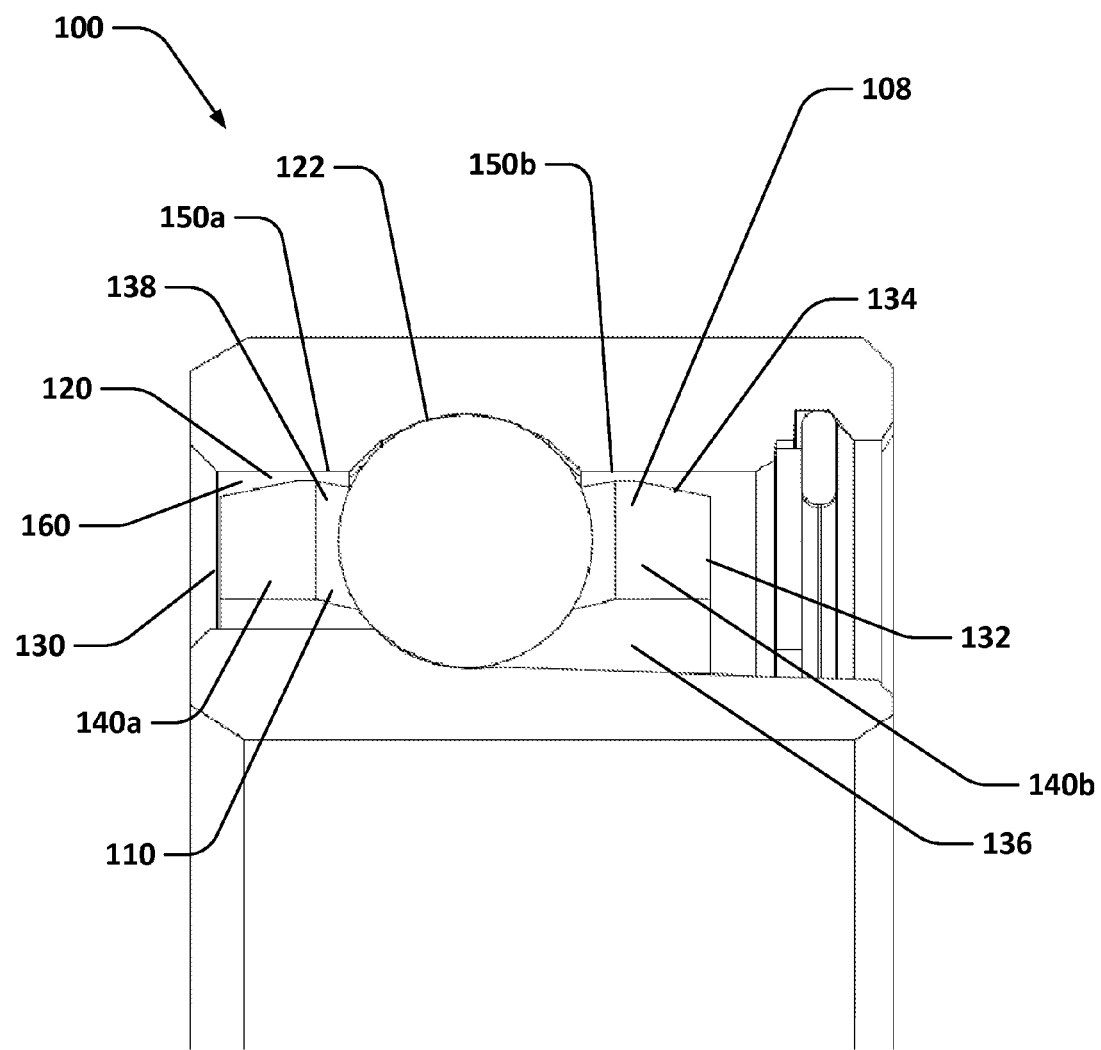
FIG. 3 is a front view of the cross-sectional view of the bearing of FIG. 1 taken along the diameter of the bearing.
Figure 4:
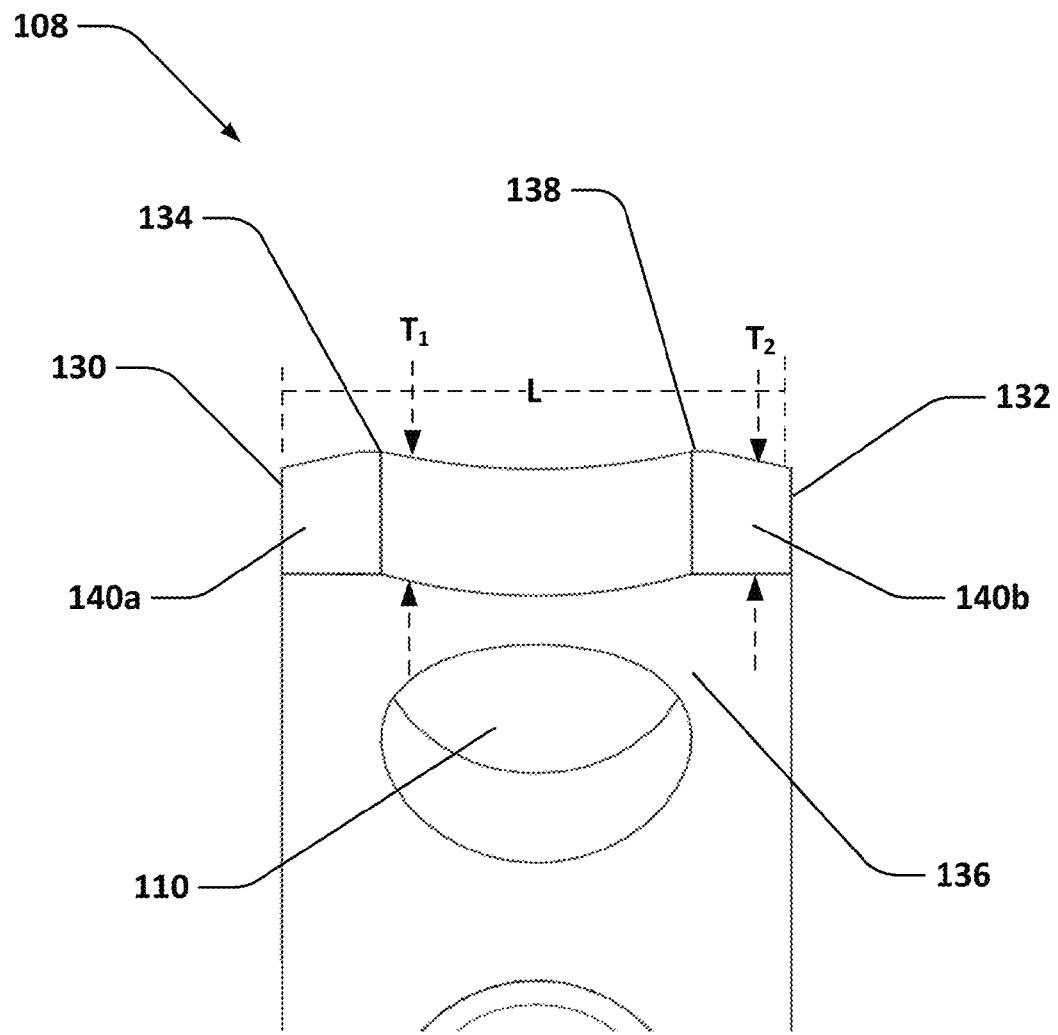
FIG. 4 is a front view of the cross-sectional view of the retainer of FIG. 1 taken along the diameter of the retainer.
Figure 5:
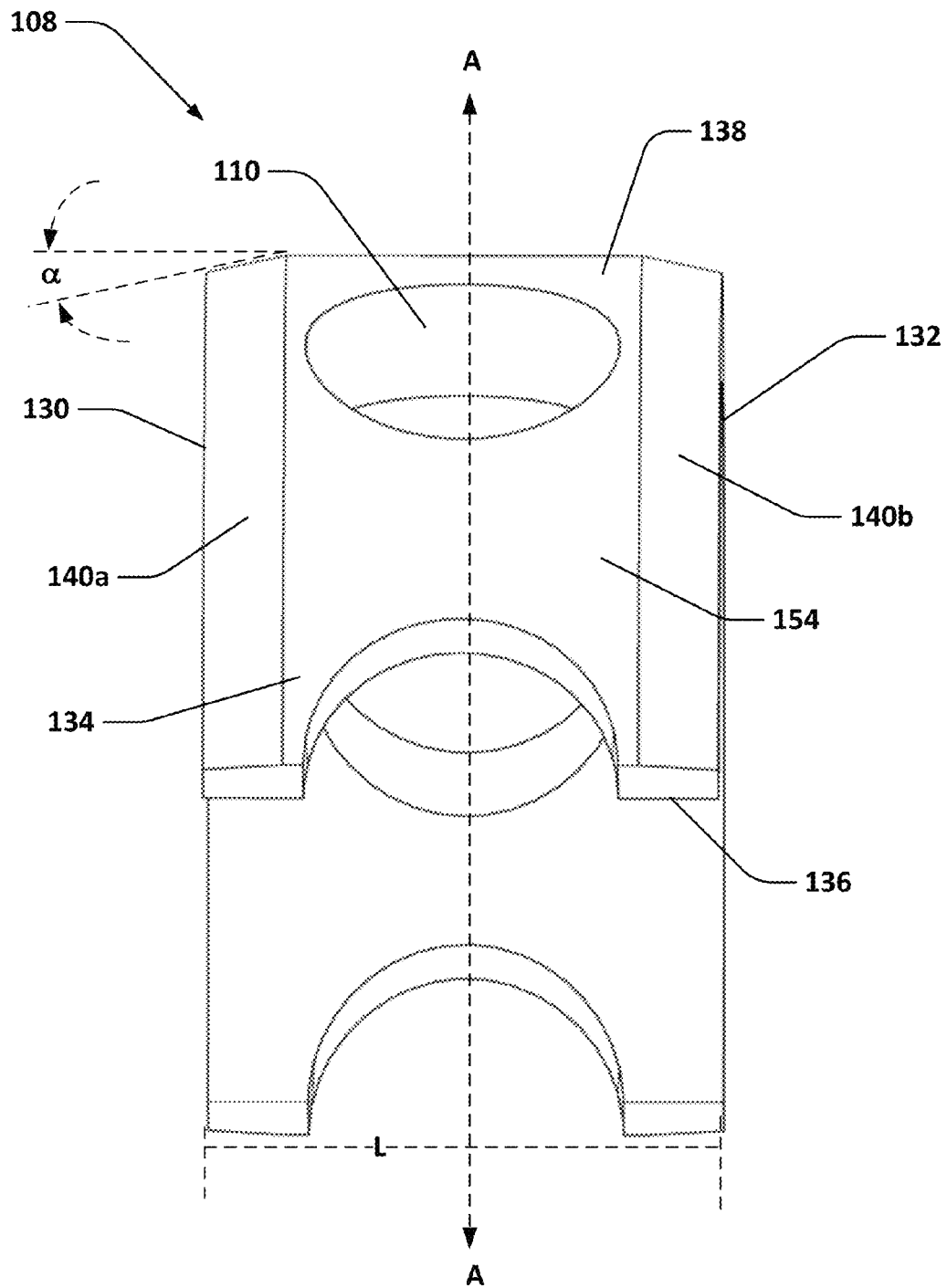
FIG. 5 is front-top perspective view of the cross-section of the retainer of FIG. 1 taken along the diameter of the retainer.

FIGS. 3, 4, and 5 illustrate an embodiment of a retainer 108. The retainer 108 includes a first side 130 and a second side 132 opposing the first side. In addition, the retainer 108 includes an outer surface 134 extending between the first side and the second side and an inner surface 136 extending between the first side 130 and the second side 132 opposing the outer surface.

Figure 7:
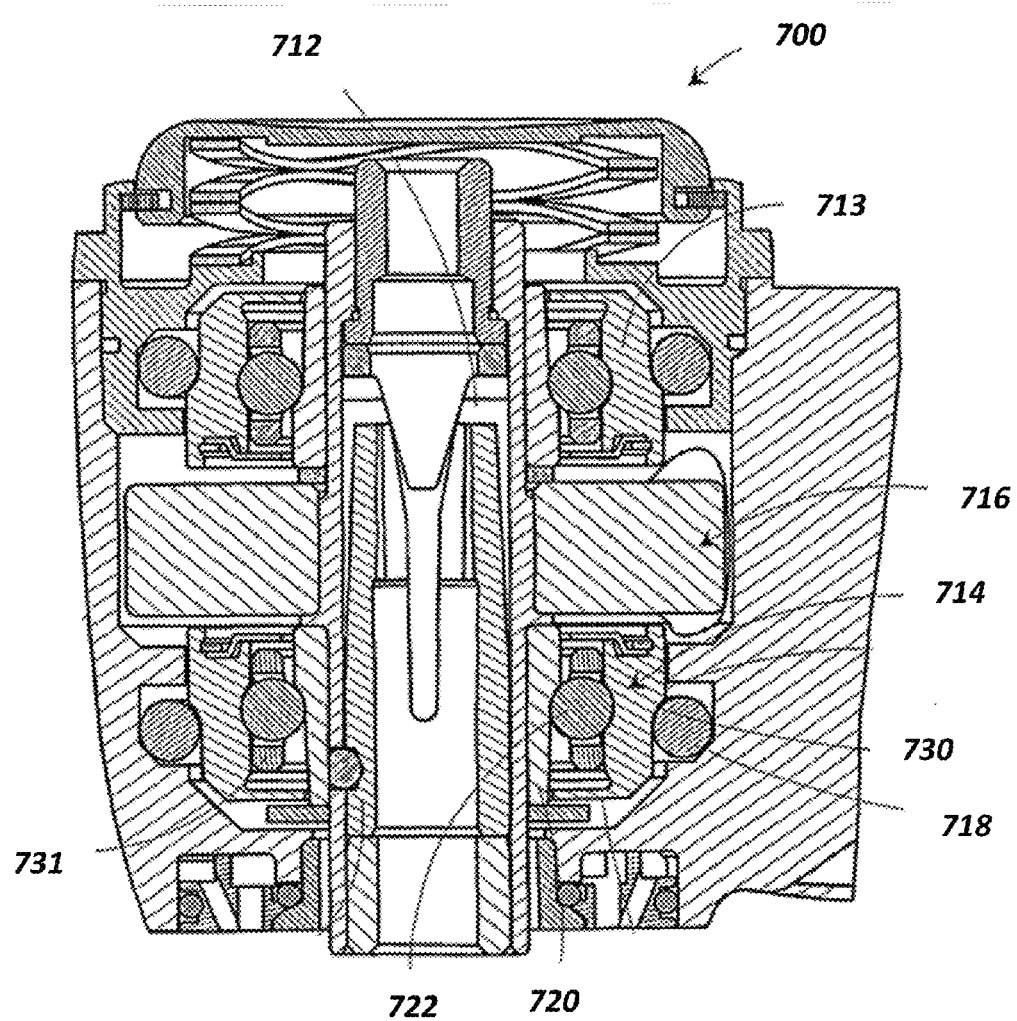
FIG. 7 illustrates a cross-section of an example of a dental handpiece in which the ball bearings herein may be incorporated.

The outer surface 134 and inner surface 136 define a central portion 138 having a first thickness $T_1$, and tapered portions 140a, 140b each having a second thickness $T_2$. The outer surface 134 of the central portion 138 of the retainer may be cylindrical in shape. The tapered portions 140a, 140b extend from each side to the central portion 138. In addition, the tapered portions extend along up to 56% of the length L of the width of the retainer between the retainer sides 130, 132 including all values and ranges from 11% to 56%, 11% to 40% along the length L of the outer surface 134, i.e., is the width of the retainer between the retainer sides 130, 132. For example, each tapered portion may extend from each side 130, 132 along up to 28% of the length L of the width being the distance between the first side and the second side, including all values and ranges from 5.5% to 28% of the length L, such as 5.5%, 6.0%, 6.5%, 7.0%, 7.5%, 8.0%, 8.5%, 9.0%, 9.5%, 10.0%, 10.5%, 11.0%, 11.5%, 12.0%, 12.5%, 13.0%, 13.5%, 14.0%, 14.5%, 15.0%, 15.5%, 16.0%, 16.5%, 17.0%, 17.5%, 18.0%, 18.5%, 19.0%, 19.5%, 20.0%, 20.5%, 21.0%, 21.5%, 22.0%, 22.5%, 23.0%, 23.5%, 24.0%, 24.5%, 25.0%, 25.5%, 26.0%, 26.5%, 27.0%, 27.5%, and 28.0%, and preferably from 5.5% to 28%, 5.5% to 20%, 6.0% to 20%, 10% to 20%, etc. Furthermore, referring to FIG. 3, the tapered portions 140a, 140b taper towards the inner surface 136 of the retainer and away from the inner diameter surface of the outer ring. The thickness of the tapered portions 140a, 140b, i.e., the second thickness $T_2$, is less than the thickness of the central portion, i.e., the first thickness $T_1$ wherein $T_2<T_1$. Further, in embodiments, the thickness $T_2$ of the tapered portions becomes smaller approaching the sides. Due to the tapered design, the retainer maintains piloting capabilities, yet operates with a relatively lower sliding friction, particularly as compared to retainers as shown in FIG. 7 which illustrates a taper that fails to extend along at least 11% of the length L of the outer surface.

In embodiments, the tapered portions 140a, 140b are symmetrical relative to an axis A-A which axis is orthogonal to the outer surface 134 of the retainer 108. The axis A-A is also parallel to the sides 130, 132 of the bearing 100. In other embodiments, the tapered portions are asymmetric, yet still taper away from the inner diameter surface of the outer ring and towards the inner surface of the retainer. In other words, the taper on either side may taper at different angles or extend along different lengths.

In embodiments, the angle α of the taper is in the range of 20° or less, including all values and ranges therein, and preferably 10°, 11°, 12°, 13°, 14°, 15°, 16°, 17°, 18°, 19°, 20°, 10° to 15° and more preferably 13° to 14°, relative to a plane defined by the central portion 138 of the retainer as illustrated in FIG. 5.

In addition, the tapering of the retainer creates an extra space 160 (see FIG. 3) created in the bearing between the outer surface 134 of the retainer 108 and the inner diameter surface 116 of the outer ring 104. The additional space 160 may accommodate an additional volume of lubricant or contaminating particles, improving therefore bearing performance.

In embodiments, the retainer 108 is formed from a polymer material. Polymer materials include, for example, those exhibiting antifriction characteristics and may be inherently lubricious or various additives may be blended in the materials such as oils, molybdenum disulfide, graphite, hexagonal boron nitride, PTFE powder, or tungsten disulfide. Preferably, the polymer materials, include for example, polyimide (PI), polyamide imide (PAI), polyether ether ketone (PEEK), polysulfones, or epoxy resins. Such polymer materials may therefore include those that have glass transition temperature of 150° C. or higher, such as 150° C. to 350° C. Other materials may be utilized, such as a ceramic material or other inorganic materials. The use of such anti-friction materials reduces the overall wear of the bearing systems.

Figure 6:
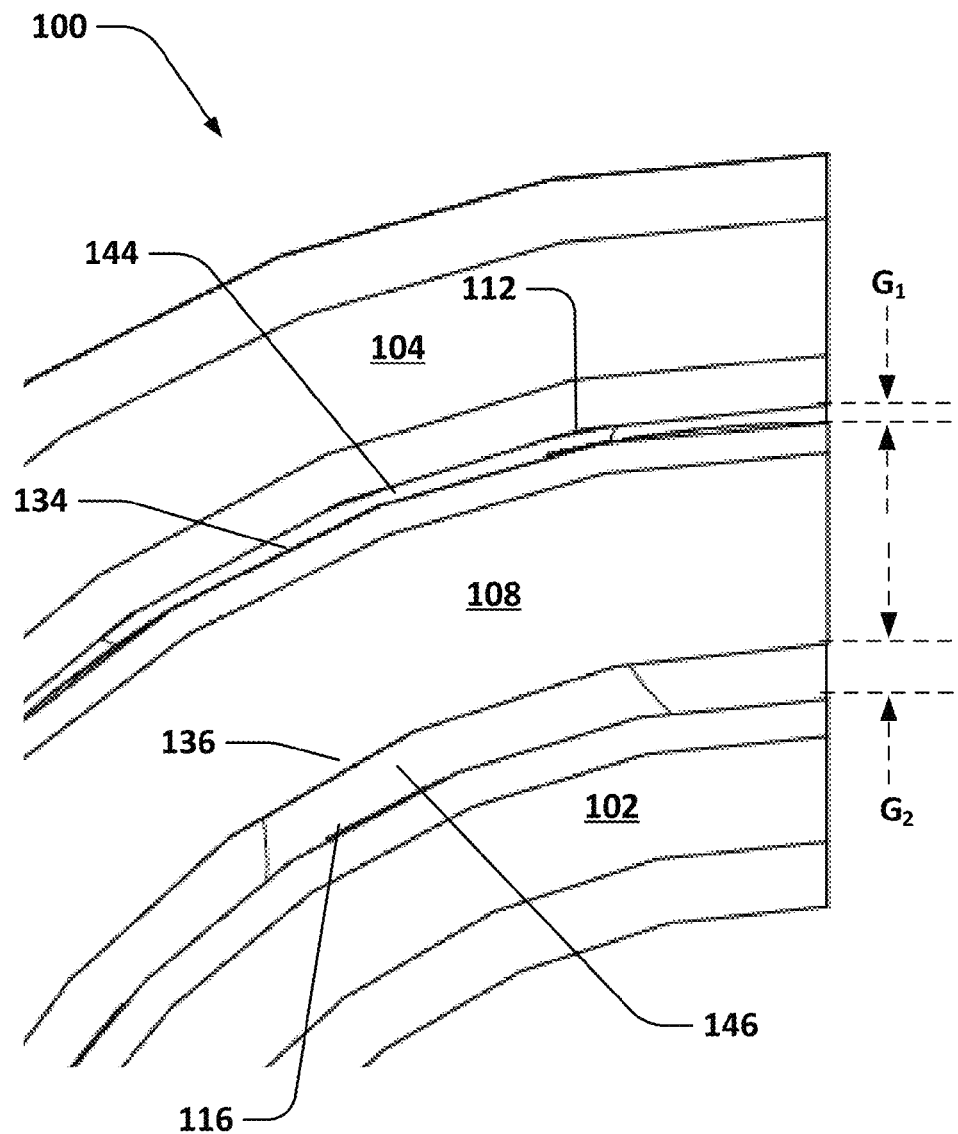
FIG. 6 is a side view of the bearing of FIG. 1 illustrating the gaps between the outer ring and retainer and the inner ring and the retainer.

Referring to FIG. 6, a first annular gap 144 is present between the inner diameter surface 112 of the outer ring 104 and the outer surface 134 of the central portion 138 of the retainer 108. A second annular gap 146 is present between the inner surface 136 of the retainer 108 and the outer diameter surface 116 of the inner ring 102. The thickness $G_1$ of the first annular gap 144 is less than the thickness $G_2$ of said second annular gap 146, wherein $G_1<G_2$. In embodiments, the thickness of the second annular gap $G_2$ is at least twice the thickness of the first annular gap $G_1$, wherein $G_2$ is in the range of (2 to 7) times $G_1$, including all values and ranges therein, such as $G_2=3*G_1$, $G_2=4*G_1$, etc. In embodiments the first annual gap 144 has a thickness in the range of 25.4 micrometers (0.001 inches) and 76.2 micrometers (0.003 inches), including all values and ranges therein, such as in the range of 25.4 micrometers (0.001 inches) and 50.8 micrometers (0.002 inches). In further embodiments, the outer ring gap (clearance) $G_1$ should be maintained between 25.4 micrometers (0.001") and 50.8 micrometers (0.002") for the retainer to be considered an outer ring piloted, which may be employed for example in a dental bearing. At the same time the inner ring clearance $G_2$ is, for example, between 127 micrometers (0.005") and 178 micrometers (0.007").

Being that the first annular gap 144 is smaller than the second annular gap, the retainer 108 is piloted, or guided by, the outer ring, wherein the inner diameter surface 120 provides piloting lands 150a, 150b on either side of the raceway 116. With the first annular gap dimensions and the wobbling, non-concentric, nature of high speed retainer motion, a cycling direct physical contact between the outer surface of the retainer and the outer ring land is present. This contact serves the purpose of limiting retainer vibration, but as may be appreciated in return, it prompts retainer wear.

Referring again to FIG. 5, a plurality of ball pockets 110 are defined through the retainer 108 connecting the inner surface 136 to the outer surface 134. As noted above, the bearing balls 106 are positioned within the ball pockets 110 in a rotatable manner. That is, the balls 106 may rotate in any direction when situated within the retainer ring 108. The retainer ring 108 spaces the balls apart around the diameter of the bearing. For example, four or more bearing balls 106 may be present, such as four to 20 bearing balls, including all values and ranges therein, such as 6, 8, 10, 12, 14, 16, etc. The interspacing of the balls depends on the number of balls present. In embodiments, the balls are interspaced equally apart. The bearing balls may be formed of a metallic material, such as heat treatable stainless steel or ceramic-type material, such as silicon nitride or cubic zirconia.

In embodiments, the plurality of ball pockets 110 are defined in the central portion 138 of the retainer 108 and preferably, are centered around the central axis A-A. Alternatively, the plurality of ball pockets are offset from the central axis A-A and are defined in both the central portion and part of the tapered portion. Further, when the ball pockets 110 are fully defined in the central portion 138, the outer surface 134 of the central portion 138 of the retainer 108 forms a land or lands 154 around and completely surrounding the plurality of ball pockets 110.

Thus it may be appreciated that in providing the tapered retainer the areas of direct retainer—outer ring contact are reduced and therefore the sliding retainer friction and wear is minimized. The lands 154 forming the relatively narrow cylindrical "belt" remain, in embodiments, immediately on the left and on the right relative to the ball pocket (i.e., through hole), providing for retainer piloting. By tapering the outer surface of the retainer, not only is wear reduced, but an extra space 160 is created allowing for the lubricant to be collected there through centrifugal forces during the bearing operation. To compensate for the retainer mechanical integrity weakening due to the reduced cross section due to the implementation of the double taper, the retainer inner diameter may be reduced as compared to a standard cylindrical retainer and the thickness of the retainer may be increased, increasing the retainer cross section and compensating for the taper. However, as noted above, the gap between the inner surface of the retainer and the outer diameter surface of the inner ring is greater than the gap between the outer surface of the retainer and the inner surface of the outer ring. For example, the outer ring gap (clearance) should be maintained between 25.4 micrometers (0.001") and 50.8 micrometers (0.002") for the retainer to be considered an outer ring piloted—for a typical dental bearing. At the same time the inner ring clearance is typically larger, for example, between 127 micrometers (0.005") and 178 micrometers (0.007").

The angular contact bearings so formed exhibit a Weibull Characteristic Life of 60 hours or greater, such as in the range of 60 to 85 hours, including all values and ranges therein, such as 65 hours, 82 hours etc., when tested according to the New Hampshire Ball Bearings accelerated life testing protocol, described further in the example below, wherein the bearings are utilized in a high speed dental handpiece subjected to rotational cycling under external load, at the speeds up to 500,000 rpm, in the conditions of marginal lubrication with repetitive sterilization at 135° C. (275° F.) until bearing failure. The angular contact bearing described herein may be incorporated into various devices and, particularly, in devices that exhibit a rotational speed of greater than 50,000 rpm, including all values and ranges therein, such as 50,000 rpm to 1,000,000 rpm, including 100,000 rpm, 500,000 rpm, etc.

In an embodiment, illustrated in FIG. 7, the angular contact bearings described herein are included in a high speed dental handpiece 700, as shown on the FIG. 7. Bearings 713 and 714 are assembled on the spindle 712 so that the air impeller 716 is positioned between the bearings. More specifically, bur side bearing 714 is supported by the rubber O-ring 718 and comprised of inner ring 720, outer ring 730, a plurality of balls 722 and the retainer 731. Accordingly, the spindle shaft 712 is received in the inner diameter of the bearing and may be retained to rotate with (and be non-rotatable to) the inner ring. The shaft or spindle 712 is configured to be coupled, either directly or indirectly, to a workpiece.

In other embodiments the angular contact bearing is included turbines, turbo-chargers, high speed electric motors, or other high speed mechanisms, wherein the bearings rotate at speeds of greater than 50,000 rpm.

EXAMPLE

Figure 8:
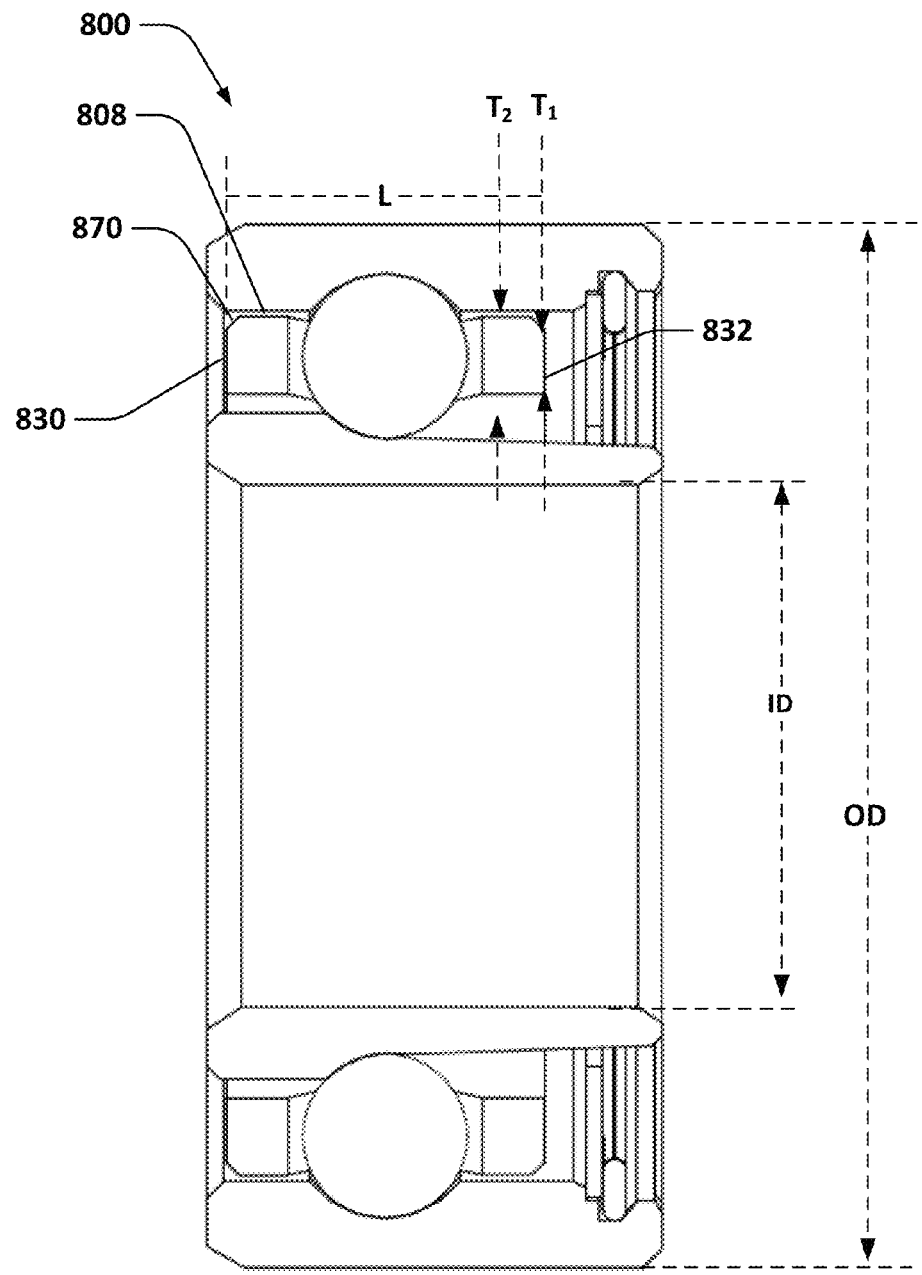
FIG. 8 illustrates a cross-section view taken along the diameter of a standard bearing.

The bearings disclosed herein were tested in comparison to a standard bearing in a high speed dental handpiece, such as that illustrated in FIG. 8. The standard bearing 800 has a 6.35 millimeter (0.25 inch) outer diameter OD (defined by the outer diameter surface of the outer ring) and a 3.175 millimeter (0.125 in) inner diameter ID (defined by the inner diameter surface of the inner ring) were assembled using the retainer with cylindrical (not tapered) outer diameter. Furthermore, the retainer 808 of the standard bearing has an overall length L from side 830 to side 832 of 1.956 millimeters (0.077 inches). Chamfers 870, each having a length of 101.6 micrometers (0.004 inches), are provided on either side of the retainer, which in combination extend along 10% of the overall length of the outer surface retainer. In addition, the retainer thickness $T_2$ in the center portion 838 of the retainer is 508 micrometers (0.020 inches) and the retainer thickness $T_1$ as between the chamfers on either edge is 406.4 micrometers (0.016 inches). Furthermore, the chamfers exhibit an angle of 45°. The standard bearing is available from New Hampshire Ball Bearing under the product number DSMDRIF-418ZOW05MCM4 A7P24LY732. The bearings disclosed herein were assembled using outer diameter rings, inner diameter rings and balls having the same specifications as the standard bearings. In addition, the retainers exhibited the same overall length. In both cases the bearings were lubricated using high-speed Minebea grease M1473 for the test purposes.

Figure 9:
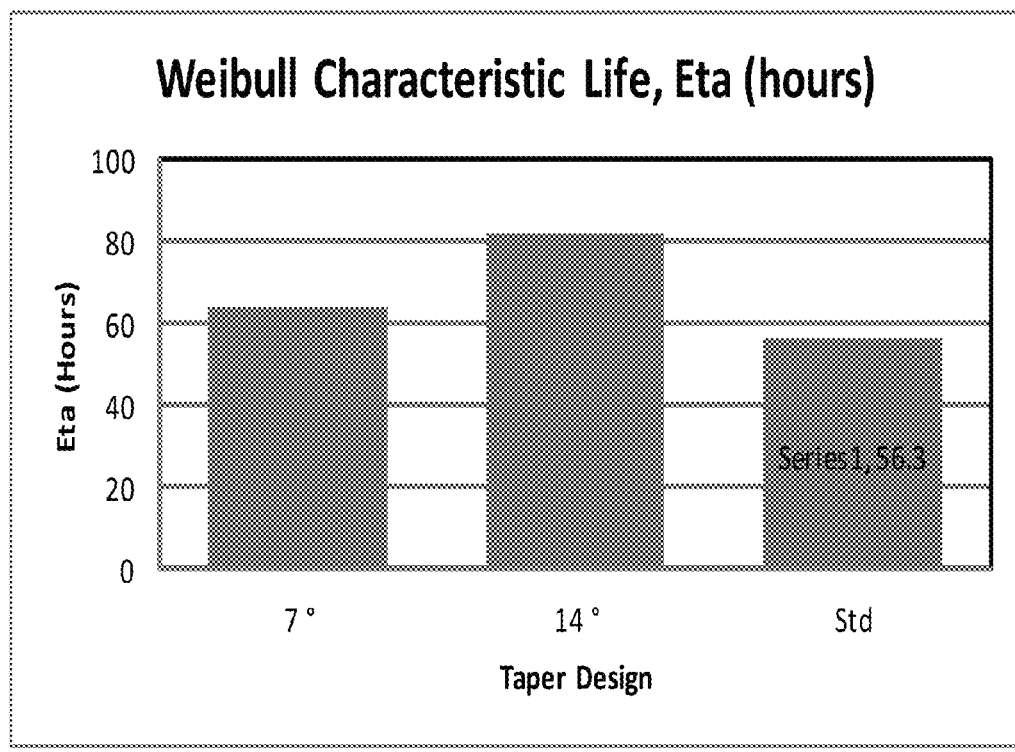
FIG. 9 illustrates a graph of statistically calculated Weibull characteristic life as a result of the series of life-cycle testing for bearing designs including a 7° taper, a 14° taper and a standard (no taper) design.

The retainer material was TORLON 4301 available from Solvay Plastics and the bearing rings and balls were made from 440C stainless steel. For three designs, ten samples each, were tested using Midwest Tradition high speed dental handpieces, available from Dentsply Midwest, Inc., including 1) the design of the present disclosure including a 7° taper, 2) the design of the present disclosure including a 14° taper and 3) bearing of standard design. Testing was performed at speeds of around 400,000 rpm at 207 kPa (30 psi) driving air pressure, a cycling side load of 142 grams (5 oz), wherein the cycling sequence is 10 seconds on, 5 second off until failure. The side load is synchronized with handpiece rotation. The hand piece was also sterilized at 135° C. (275° F.) for 30 minutes after each 1 hour of cycling. Failure is understood to occur when the speed drops over 20% below starting or initial speed. Table 1 below includes the testing data and FIG. 9 illustrates the resulting statistically analyzed data using known and common in the accelerated life testing art methods of Weibull statistical analysis and resulting in Weibull characteristic life (eta) and Weibull chart slope (beta).

TABLE 1

Weibull Characteristic Life of Bearings

| Design | Taper | Lubricant | Retainer Material | Weibull characteristic life, eta (hours) | Weibull chart slope, beta |
|---|---|---|---|---|---|
| 1 | 7° | M1473 (3 mg) | TORLON 4301 | 64.1 | 4.05 |
| 2 | 14° | M1473 (3 mg) | TORLON 4301 | 82.2 | 2.96 |
| 3 | Standard | M1473 (3 mg) | TORLON 4301 | 56.3 | 2.60 |

As seen in the data provided above, bearings with double tapered retainer implementation demonstrate near 10% life improvement in a 7° retainer taper and up to almost a 50% life improvement in a 14° retainer OD taper compared to similar bearings assembled with the standard retainers having a generally cylindrical OD.

Thus, provided herein is an angular contact high-speed ball bearing assembly using a full ball retainer guided by the outer ring land. The retainer has, in embodiments, a symmetrical tapered outer diameter facing the bearing guiding land, (i.e., the inner diameter surface of the outer ring), which forms a narrow cylindrical "belt" bordering the ball pocket (i.e., through hole) area. This reduces frication and retainer wear as opposed to cylindrical surfaces that extend across substantially the entire outer diameter as tapered retainer geometry provides for less direct contact between the retainer outer diameter (or outer surface) and the piloting surface of the bearing outer ring. Moreover, an additional space is created between the retainer outer surface and guiding surface allowing for more of conventional lubricant to be accommodated therein as compared with traditional cylindrical outer diameter retainer shape.

The foregoing description of several methods and embodiments has been presented for purposes of illustration. It is not intended to be exhaustive or to limit the claims to the precise steps and/or forms disclosed, and obviously many modifications and variations are possible in light of the above teaching. It is intended that the scope of the invention be defined by the claims appended hereto.

What is claimed is:

1. An angular contact bearing, comprising:
an inner ring including an outer diameter surface and a raceway defined in said outer diameter surface;
an outer ring including an inner diameter surface and a raceway defined in said inner diameter surface;
a plurality of balls in rolling contact with said raceways;
a retainer piloted by the outer ring including
a first side and a second side opposing said first side, said retainer having a width being the distance between said first side and said second side,
an outer surface extending between said first side and said second side and an inner surface opposing said outer surface extending between said first side and said second side, wherein said outer surface and said inner surface define a central portion having a first thickness $T_1$ and said outer surface provides a double taper, wherein said double taper is formed by a first tapered portion that increases in thickness from said first side to said central portion and extends up to 28% of the length of said retainer width, and a second tapered portion that increases in thickness from said second side to said central portion and extends up to 28% of the length of said retainer width,
wherein said tapered portions are formed by tapering said outer surface away from said inner diameter surface of said outer ring and said inner surface is flat,
wherein said tapered portions each having a second thickness $T_2$,
wherein each tapered portion is tapered at an angle of 20° or less relative to said central portion, and
said second thickness $T_2$ is less than said first thickness $T_1$,
wherein a first annular gap $G_1$ is present between said outer ring and said outer surface of said central portion of said retainer and a second annular gap $G_2$ is present between said inner surface of said retainer and said inner ring, wherein the thickness of said first annular gap $G_1$ is less than the thickness of said second annular gap $G_2$; and
a plurality of through holes defined in said retainer, wherein one of said balls is positioned in each of said through holes in a rotatable manner.

2. The angular contact bearing of claim 1, wherein said tapered portions are symmetrical relative to an axis orthogonal to said outer surface of said retainer.

3. The angular contact bearing of claim 1, wherein said outer surface of said central portion of said retainer is cylindrical.

4. The angular contact bearing of claim 1, wherein said plurality of through holes are defined in said central portion of said retainer.

5. The angular contact bearing of claim 4, wherein said outer surface of said central portion of said retainer forms a land around said plurality of through holes.

6. The angular contact bearing of claim 1, wherein said tapered portions of said outer surface taper at an angle of 13° to 14° relative to said central portion.

7. The angular contact bearing of claim 1, wherein said retainer is formed from a polymer material.

8. The angular contact bearing of claim 7, wherein said polymer material includes an additive selected from the group of oils, molybdenum disulfide, graphite, hexagonal boron nitride, polytetrafluoroethylene (PTFE) powder, or tungsten disulfide.

9. The angular contact bearing of claim 7, wherein said polymer material is selected from the group of polyimide, polyether ether ketone, polysulfone, or epoxy resin.

10. The angular contact bearing of claim 1, wherein said retainer is formed from polyamide imide.

11. The angular contact bearing of claim 1, wherein said plurality of balls are formed from steel.

12. The angular contact bearing of claim 1, wherein said plurality of balls are formed from ceramic.

13. The angular contact bearing of claim 1, wherein an average gap in the range of 25.4 micrometers (0.001 inches) to 76.2 micrometers (0.003 inches) is present between said inner diameter surface of said outer ring and said outer surface of said central portion of said retainer.

14. A device comprising a bearing that rotates at speeds higher than 50,000 RPM where said bearing comprises the angular contact bearing of claim 1.

15. A turbine comprising the angular contact bearing of claim 1.

16. A turbo-charger comprising the angular contact bearing of claim 1.

17. An electric motor comprising the angular contact bearing of claim 1.

18. The electric motor of claim 17, wherein said motor is configured to rotate at speeds of greater than 50,000 rpm to 1,000,000 rpm.

19. An angular contact bearing, comprising:
an inner ring including an outer diameter surface and a raceway defined in said outer diameter surface;
an outer ring including an inner diameter surface and a raceway defined in said inner diameter surface;
a plurality of balls in rolling contact with said raceways;
a retainer piloted by the outer ring including
a first side and a second side opposing said first side, said retainer having a width being the distance between said first side and said second side,
an outer surface extending between said first side and said second side and an inner surface opposing said outer surface extending between said first side and said second side, wherein said outer surface and said inner surface define a central portion having a first thickness $T_1$ and said outer surface provides a double taper, wherein said double taper is formed by a first tapered portion that increases in thickness from said first side to said central portion and extends at least 11% of the length of said retainer width, and a second tapered portion that increases in thickness from said second side to said central portion and extends at least 11% of the length of said retainer width,
wherein said tapered portions are formed by tapering said outer surface away from said inner diameter surface of said outer ring and said inner surface is flat,
wherein said tapered portions each having a second thickness $T_2$,
said second thickness $T_2$ is less than said first thickness $T_1$,
wherein a first annular gap $G_1$ is present between said outer ring and said outer surface of said central portion of said retainer and a second annular gap $G_2$ is present between said inner surface of said retainer and said inner ring, wherein the thickness of said first annular gap $G_1$ is less than the thickness of said second annular gap $G_2$; and
a plurality of through holes defined in said retainer, wherein one of said balls is positioned in each of said through holes in a rotatable manner.

20. The angular contact bearing of claim 19, wherein said tapered portions of said outer surface taper at an angle of 20° or less relative to said central portion.

21. A dental device comprising:
an angular contact ball bearing including
an inner ring including an outer diameter surface and a raceway defined in said outer diameter surface,
an outer ring including an inner diameter surface and a raceway defined in said inner diameter surface,
a plurality of balls in rolling contact with said raceways,
a retainer piloted by the outer ring including a first side and a second side opposing said first side, said retainer having a width being the distance between said first side and said second side, an outer surface extending between said first side and said second side, and an inner surface opposing said outer surface extending between said first side and said second side, wherein said outer surface and said inner surface define a central portion having a first thickness $T_1$ and said outer surface provide a double taper, wherein said double taper is formed by a first tapered portion that increases in thickness from said first side to said central portion and extends up to 28% of the length of said retainer width, and a second tapered portion that increases in thickness from said second side to said central portion and extends up to 28% of the length of said retainer width,
wherein said tapered portions each having a second thickness $T_2$,
wherein said tapered portions are formed by tapering said outer surface away from said inner diameter surface of said outer ring and said inner surface is flat,
wherein each tapered portion is tapered at an angle of 20° or less relative to said central portion,
said second thickness $T_2$ is less than said first thickness $T_1$,
wherein a first annular gap $G_1$ is present between said outer ring and said outer surface of said central portion of said retainer and a second annular gap $G_2$ is present between said inner surface of said retainer and said inner ring, wherein the thickness of said first annular gap $G_1$ is less than the thickness of said second annular gap $G_2$; and
a plurality of through holes defined in said retainer, wherein one of said balls are positioned in each of said through holes in a rotatable manner; and
a shaft received in said inner ring configured to be coupled to a workpiece.

* * * * *